(12) United States Patent
Dornelas et al.

(10) Patent No.: US 6,822,139 B1
(45) Date of Patent: Nov. 23, 2004

(54) MODULATION OF STORAGE ORGANS

(75) Inventors: Marcelo Dornelas, B. Colinos (BR); Andre A. M. van Lammeren, Wageningen (NL); Martin Kreis, Orsay (FR)

(73) Assignee: Advanta Seeds, B.V., Kapelle (NL)

( * ) Notice: Subject to any disclaimer, the term of this patent is extended or adjusted under 35 U.S.C. 154(b) by 0 days.

(21) Appl. No.: 09/578,194

(22) Filed: May 24, 2000

(51) Int. Cl.[7] .......................... A01H 1/00; A01H 11/00; C12N 15/82; C12P 19/34; C07H 21/04
(52) U.S. Cl. .................... 800/278; 435/91.1; 435/91.31; 435/468; 536/23.1; 536/24.5; 800/295
(58) Field of Search .................. 435/6, 91.1, 91.3, 435/468, 410, 91.31; 536/23.1, 24.5, 23.6, 426, 470, 410, 419, 430, 378, 24.1; 800/278, 295, 287, 290, 292, 293

(56) References Cited

PUBLICATIONS

MC Dornelas et al., The Plant Journal."Arabidopsis thaliana SHAGGY–related protein kinases (AtSK11 and 12) function in perianth and gynoecium development," 2000, 21(5), 419–429.*

HL Piao et al. Plant Physiology "An Arabidopsis GSK3/shaggy–Like Gene that Complements Yeast Salt Stress–Sensitive Mutants is Induced by NaCl and Abscisic Acid," Apr. 1999, vol. 119, pp. 1527–1534.*

Dornelas, et al., Three New cDNAs Related to SGG/GSK–3 (Shaggy/Glycogen Synthase Kinase—3) from Arabidopsis thaliana (Acccession No. X94938, X94939 and X99696 (PGR97–008); Plant Physiol., vol. 113, Issue 1, p. 306 (Jan. 1997).

G. Tichtinsky et al, "An evolutionary conserved group of plant GSK–3/shaggy–like protein kinase genes preferentially expressed in developing pollen", Biochimica et Biophysica Acta 1442, pp. 261–273 (1998).

Dorenelas, et al., "Characterization of three novel members of the Arabidopsis SHAGGY–related protein kinase (ASK) multigene family", Plant Molecular Biology, 39:137–147, (1999).

Bechtold, N., Ellis, J., and Pelletier, G., "In planta Agrobacterium mediated gene transfer by infiltration of adult Arabidopsis Thaliana plants", Genetics, pp. 1–16.

Dornelas, M., Lejueune, B., Dron, M., Kreis, M., "The Arabidopsis SHAGGY–related protein kinase (ASK) gene family structure, organization and evolution", Gene 212, pp. 249–257 (1998).

Bouchez, et al., "A binary vector based on Basta resistance for in planta transformation of Arabidopsis thaliana", Genetics, pp. 1–18.

Claudia Jonak,Wound –Induced Expression and Activation of WIG,a Novel Glycogen Synthase Kinase 3, The Plant Cell, vol. 12 1467–1475, Aug. 2000.

* cited by examiner

Primary Examiner—Ram R. Shukla
Assistant Examiner—Jane Zara
(74) Attorney, Agent, or Firm—Dana S. Rewoldt

(57) ABSTRACT

The present invention relates to a process for the production of transgenic plants capable of forming seeds whose embryos exhibit a more refined development.

22 Claims, 2 Drawing Sheets

MODULATION OF STORAGE ORGANS

DESCRIPTION

The present invention relates to a process for the production of a transgenic plant the seeds of which form embryos that exhibit a modified development and to seeds, plant derived tissues and plants obtained thereby.

The present invention relates to plant genetic engineering. A goal of plant genetic engineering is to introduce desired genes into a plant in such a manner that these genes will be functional in the desired tissue at the correct time. Plant genetic engineering aims for instance to modify the pathways of primary and secondary metabolites of economic importance including the cellular and organic optimisation of compounds. Furthermore, plant genetic engineering aims to insert and develop mechanisms of resistance against physical, chemical and biological stress factors. Finally, plant genetic engineering aims to alter the development of plants and their seeds. Altering the developmental pattern of a plant enables for instance the production of plants with a modified plant or organ morphology. In particular, it is desired to engineer plants and plant seedlings exhibiting a modified, in particular increased number of storage organs such as cotyledons. These storage organs may contain valuable and commercially interesting substances such as proteins, polysaccharides, globoides, and vegetable oils, such as seed storage lipids of higher plants. It is also desirable to provide genetically engineered plants producing abortive seed for use in breeding programs and for agricultural purposes.

Genes involved in cell division, signal transduction pathways, establishment of cell fate and pattern formation have been extensively studied, since they are of general importance to the understanding of plant development. The Arabidopsis SHAGGY-related protein kinase (ASK) multigene family calls for proteins that share a highly conserved catalytic protein kinase domain being about 70% identical to animal genes known to be involved in signal transduction pathways controlling patterning cell fate determination and cytokinases (Dornelas et al., Gene 212 (1998), 249–257). The ASK proteins are believed to be involved in signal transduction pathways that establish cell fate and/or pattern formation in plants. The ASK gene family comprises various members, such as ASK alpha α, gamma γ, dzeta ζ, etha η and iota ι.

Although cDNA and genomic DNA sequences of these genes are available, the function of these genes during the development of the plant is still unknown (Dornelas et al., Plant Molecular Biology 39 (1999), 137–147, Tichtinsky et al., Biochimica et Biophysica Acta 1442 (1998), 261–273). In fact, speculations on their function are only based on sequence similarities of the encoded products to animal counterparts. Up until now, it is not known whether these genes might prove useful in plant genetic engineering and, should this be the case, forwhich purpose.

Thus, the technical problem underlying the present invention is to provide plants which exhibit improved properties that increase their commercial value.

The present invention solves this problem by providing a process for the production of a transgenic plant the seeds of which comprise an embryo exhibiting a modified development, wherein at least one plant cell is transformed with at least one DNA construct comprising a nucleic acid sequence derived from at least one ASK-gene of group II and regenerated to a plant whose embryos exhibit the modified development. The problem is also solved by plants and seeds produced by this process, and plants and seeds comprising an expressible DNA construct containing an ASK-gene of group II.

The present invention relates to the unexpected teaching that a particular ASK-gene which encodes a kinase may be used to specifically alter the development of a plant embryo and/or architecture of a plant. Thus, the present invention foresees the use of a DNA construct comprising a nucleic acid sequence derived from at least one ASK-gene of group II for genetically modifying a plant, whereby a plant with advantageous properties is obtained. Such a DNA construct may be a sense or an antisense construct or a construct comprising a transposable element such as En/Spm or Ac/Ds. According to the present invention, the transposable element transformed into a plant cell is capable of inactivating an endogenous ASK-gene of group II so as to generate plants which produce embryos exhibiting a modified development. In the context of the present invention, a sense construct comprises at least one regulatory element being functionally linked in sense orientation, i.e. wild-type orientation, to a nucleic acid sequence derived from at least one ASK-gene of group II. In a particularly preferred embodiment, the ASK-gene derived sequence is the coding sequence of an ASK-gene of group II. Such a construct may be used to overexpress the coding sequence of an ASK-gene of group II. Such a construct may be particularly useful for a co-suppression technology, wherein at least one transgenic copy of an ASK-gene of group II is inserted into the genome of a target plant cell and wherein due to a high copy number of such a transgenic DNA sequence and/or an increased expression rate, down regulation of an endogenous corresponding ASK-gene can be achieved. In the context of the present invention, the term co-suppression construct refers to such a construct comprising at least one regulatory element being functionally linked in sense orientation to a nucleic acid sequence derived from an ASK-gene of group II, in particular a transcribed region, most preferably a coding region.

The invention also relates to down regulation of expression of an endogenous ASKene of group II by using antisense technology. Thus, in one preferred embodiment of the present invention, a DNA construct is used, wherein at least one regulatory element is operably linked in antisense orientation to a nucleic acid sequence derived from at least one ASK-gene of group II, in particular a transcribed region or a part thereof, in particular the coding sequence or a part thereof. In the context of the present invention, antisense orientation refers to a non-wild-type orientation of a 5' regulatory element, that is a promoter to its coding sequence, in particular an orientation wherein from a given functional regulatory 5' element, the antisense strand of the ASK-gene of group II is transcribed.

As explained above, the DNA construct may also comprise a transposable element which is capable of being inserted in an endogenous ASK-gene of group II, thereby inactivating this gene.

The process of the present invention enables the production of transgenic plants producing seeds whose embryos exhibit a modified development. In a particularly preferred embodiment of the present invention, the embryo generated within the seed of the transgenic plant of the present invention is unexpectedly characterised by the development of an increased number of cotyledons in contrast to wild-type plants. Accordingly, in that case where the plant cell transformed is a plant cell obtained from a monocotyledonous plant, the present invention enables the production of seeds whose embryos will develop 2, 3, 4 or even more cotyledons. In the case where the plant cell transformed is a plant cell obtained from a dicotyledonous plant, the present invention enables the production of seeds whose embryos will develop 3, 4, 5 or even more cotyledons. Thus, the present invention enables the production of polycotyledonous plants. These plants and in particular their embryos and seedlings are advantageous in so far as they may contain, due to their increased number of cotyledons, an increased amount of valuable and commercially interesting substances, such as proteins or vegetable oils. Thus, the plant of the present invention may advantageously be used as plants producing in their storage organs, in particular their cotyledons, commercially interesting substances. The process of the present invention enabling the generation of polycotyledonous plants is also useful for the production of plants having additional leaves, flowers and/or male or female reproductive organs. Such plants may advantageously be ornamental plants. These plants may be plants being transgenic not only for the nucleic acid sequence derived from the ASK-gene of group II, but also for other genes, such as ASK genes of group I or III. These other genes may code for the tissue-specific, in particular cotyledon-specific expression of valuable substances.

In another preferred embodiment of the present invention, the seeds are characterised by an abortive development of the embryo. Accordingly, the embryos of the seed will not develop properly and will finally abort. In this particular embodiment of the present invention, the seed contains essentially or exclusively endosperm tissue, since the embryo fails to properly develop and aborts after a few cell divisions. Therefore, no or virtually no differentiated embryo cells are present in the seed, so that the seed contains little or no embryo oils and accordingly exhibits no rancid problems. Thus, the seeds of the present invention provide an increased storage stability and shelf-life. The seed of plants generated according to the present invention may be used advantageously for starch production, in particular of a more homogeneous starch composition, and/or the production of useful new or increased amounts of compounds in the endosperm. The seeds of the present invention therefore allow the production of such compounds in higher purity and facilitate their simplified isolation.

In a particularly preferred embodiment, the nucleic acid sequence derived from an ASK-gene is an ASKdzeta or an ASKetha gene. ASK is the abbreviation for Arabidopsis SHAGGY-related protein kinases (Dornelas et al., 1998). The cDNA and genomic DNA sequences of various ASK-gene, including the ASK-genes of group II, are published in Dornelas et al. Gene 212 (1998), 249–257 and Dornelas et al. Plant Molecular Biology 39, (1999) 137–147. This article contains the reference to Accession X94938 in the GenBank. The Arabidopsis thaliana mRNA for shaqqy-like Kinase Dzeta identified as Accession X94938 is provided herein as Seq. Id. No. 6. In the context of the present invention, ASK-genes of group II are the ASK genes classified according to Dornelas et al. (199) in group II of SGG/GSK-3 homologues, in particular ASKiota, ASKdzeta and ASKetha. In a particularly preferred embodiment, the ASK-genes of group II of the present invention are ASKdzeta and ASKetha genes.

According to the present invention, the DNA constructs, in particular the antisense and sense constructs used, comprise a nucleic acid sequence derived from an ASK-gene of group II, in particular the ASKdzeta and/or ASKetha gene, or parts thereof.

In a preferred embodiment of the present invention, the use of the ASKdzeta gene in antisense constructs or in sense constructs used from instance in co-suppression technology (co-suppression constructs) for eliminating wild-type seeds, whose embryos and seedlings are characterized by the development of, in contrast to that of a wild-type plant, an increased number of cotyledons obviously caused, without being limited by theory, by abnormal divisions of the hypophyseal cell and abnormal development of the upper and lower tiers of the embryo. As a consequence, the embryo and seedling exhibits supernumerary cells and shows polycotyly.

In a further preferred embodiment of the present invention, the use of the ASKetha gene in the antisense construct or in sense constructs used in co-suppression technology for eliminating wild-type ASKetha expression enables the production of plants whose seeds are characterised by an abnormal development in the course of which the embryo aborts. In ASKetha antisense or co-suppressed embryos the suspensor cells divide abnormally leading to embryo abortion, in particular at the globular stage.

In a further preferred embodiment, it is contemplated to use both ASKdzetha and ASKetha genes in the antisense or co-suppression construct of the present invention enabling the production of a transgenic plant the embryos of which are characterised by an abnormal development, in the course of which embryos containing both ASKdzetha and ASKetha antisense or co-suppression construct fail to form a distinct suspensorlembryo proper structure and abort, preferably already after a few cell divisions. Accordingly, the use of ASKdzetha and ASKetha genes together in an antisense or co-suppression construct enables the production of plants, the seeds of which are characterised by the abortion of the embryo as well.

The present invention also relates to processes to restore the antisense effect obtained by using the antisense construct mentioned above. To be able to restore the antisense effect, a further DNA construct comprising an ASK-gene derived nucleic acid sequence in sense orientation under control of a switchable or inducible promoter could be used to transform the plant. After switching on the promoter, the antisense effect will be restored. Another method for restoring the above described elimination effect is to utilise a DNA construct, in particular an antisense or co-suppression construct employing an inducible promoter to control the expression of the nucleic acid sequence derived from an ASK-gene of group II, in particular in the antisense or co-suppression construct, via external factors.

In a particularly preferred embodiment, the nucleic acid sequence derived from an ASKgene of group II is used in the form of an ASK cDNA or ASK genomic DNA, being autologous or heterologous to the plant cell to be transformed. Thus, it is possible to use only the transcribed, in particular the coding sequences or part of the transcribed or coding sequences of the ASK-gene of group II. In a preferred embodiment of the present invention, the nucleic acid sequence derived from an ASK-gene of group II is a fragment of 150–350 base pairs, in particular of about 300 base pairs, corresponding to the 5' untranslated region and part of the N-terminal coding region of ASK-genes of group II. However, it is also possible to use other fragments of the ASK-genes both in cDNA or genomic form. In particular, it is also possible to use parts of the ASK-genes which are outside of the coding region, as long as their use in the DNA construct of the present invention interferes, in particular inhibits the expression of the endogenous ASK-genes of the plant cell transformed.

In a particularly preferred embodiment of the present invention, the nucleic acid sequence derived from an ASKgene used in the present DNA construct may be obtained using PCR. In the following, the above identified ASK-sequences are also called ASK-gene derived nucleic acid sequences, which term is used synonymously with the term ASK-gene of group II.

In a preferred embodiment of the present invention, the ASK-derived nucleic acid sequence is operably linked in antisense orientation to at least one regulatory element for directing the expression of the nucleic acid sequence, preferably in plant cells such as monocot or dicot cells. Such a combined nucleic acid sequence represents the antisense construct of the present invention and may be cloned into a suitable vector, thus comprising any one of the ASK derived nucleic acid sequences mentioned above. However, the present invention also relates to DNA constructs comprising at least one ASK-derived nucleic acid sequence operably linked in sense orientation to at least one regulatory element.

The present invention preferably contemplates, as regulatory elements, elements that direct or enhance, in particular tissue specific, expression in cells containing the above DNA construct. These regulatory elements may be located 5', 3' or 5' and 3' of the ASK-gene derived nucleic acid sequences, in particular the coding sequence, of the present invention. Of course, for instance in the case where a genomic DNA clone according to the present invention is used in the sense or antisense construct, additional regulatory elements may also be present within the nucleic acid sequence of the present invention, in particular within an intron. However, the regulatory element may also be an intron in its entirety.

The present invention relates in a preferred embodiment to the above mentioned vector wherein the 5' regulatory element is a transcription initiation region, preferably a plant promoter, in particular the 35S CaMV promoter. However, depending upon the host and/or target tissue, the regulatory 5' element will vary and may include other regions from viral, plasmid or chromosomal genes. These genes may be derived from *E. coli*, *B. subtilis*, yeast or the like. Of course, other regulatory elements functional in plants, e.g. from plant genes, *Agrobacterium tumefaciens* and/or *A.rhizogenes* genes may be used as well. The promoters may be of inducible, regulatable, or constitutive nature. The promoter may also encompass 5' untranslated regions from foreign genes and/or translation initiation sequences. The invention relates in a particularly preferred embodiment to the use of the FBP7 and/or FBP 11 promoter from Petunia (Rounsley et al. (1995); Angenent et al. (1995)) or the LTP-promoter (Thoma et al. (1994)).

Further examples of promoters to be used in the context of the present invention are the cauliflower mosaic virus (CaMV) 19S promoter, nopaline synthase promoters, pathogenesis-related (PR) protein promoters, the ubiquitin promoter from maize for a constitutive expression, the HMG promoters from wheat, promoters from Zein genes from maize, small subunit of ribulose bisphosphonate carboxylase (ssuRUBISCO) promoters, the 35S transcript promoter from the figworm mosaic virus (FMV 35S), the octopine synthase promoter or the actin promoter from rice etc. It is preferred that the particular promoter selected should be capable of causing sufficient expression to result in the production of an effective amount of antisense or sense mRNA or modified or wild-type kinase to interfere with embryo development. Of course, for selective expression tissue or organ specific promoters e.g. Petunia FBP 11 may be used.

The DNA construct of the invention may contain multiple copies of a promoter andlor multiple copies of the ASK-gene derived nucleic acid sequences. In addition, the construct may include coding sequences for markers and coding sequences for other peptides such as signal or transit peptides or resistance genes for instance against virus infections or antibiotics.

Useful markers are peptides providing antibiotic or drug resistance, for example resistance to phosphinotrycine, hygromycin, kanamycin, G418, gentamycin, lincomycin, methotrexate or glyphosate. These markers, such as the herbicide resistance gene pat encoding a phosphinotrycine acetyl transferase, can be used to select cells transformed with the chimeric DNA constructs of the invention from untransformed cells. Of course, other markers are markers coding peptidic enzymes which can be easily detected by a visible reaction, for example a colour reaction such as luciferase, β-1,3-glucuronidase or β-galactosidase.

Signal or transit peptides provide the kinase formed on expression of the DNA constructs of the present invention with the ability to be transported to the desired site of action. Examples for transit peptides of the present invention are chloroplast transit peptides, mitochondria transit peptides or nuclear localisation signals.

In DNA constructs containing coding sequences for transit peptides, these sequences are usually derived from a plant, for instance from corn, potato, Arabidopsis or tobacco. Preferably, transit peptides and coding sequences are derived from the same plant. In particular such a DNA construct comprises a DNA sequence derived from an ASK-gene of group II and a DNA sequence coding for a transit peptide operably linked to a promoter, wherein said promoter is different from the promoter linked to said coding sequences in wild-type genes, but functional in plant cells. In particular, said promoter provides for higher transcription efficiency than the wild-type promoter.

The mRNA produced by a DNA construct of the present invention may advantageously also contain a 5' non-translated leader sequence. This sequence may be derived from the promoter selected to express the gene and can be specifically modified so as to increase translation and stability of the mRNA. The 5' non-translated regions can also be obtained from viral RNAs from suitable eucaryotic genes or a synthetic gene sequence.

Preferably, the coding sequence of the present invention is not only operably linked to 5' regulatory elements, such as promoters, but is additionally linked to other regulatory elements, such as enhancers and/or 3' regulatory elements. For instance, the vectors of the present invention may contain functional terminator sequences such as the terminator of the octopine synthase gene from *Agrobacterium tumefaciens*. Further 3' non-translated regions to be used in a chimeric construct of the present invention to cause the addition of polyadenylate nucleotides to the 3' end of the transcribed RNA are the polyadenylation signals of the *Agrobacterium tumefaciens* nopaline synthase gene (NOS) or from plant genes such as the soy bean storage protein gene and the small subunit of the ribulose-1,5-bisphosphonate carboxylase (ssuRUB-ISCO) gene.

Of course, the present invention also relates to vectors described above, which furthermore contain further regulatory elements and/or elements necessary for the stable and/or transient integration of the nucleic acid sequence of the present invention into the genome of a host, for instance T-DNA sequences, in particular the left, the right, or both T-DNA border sequences. In a particularly preferred embodiment of the present invention, the nucleic acid sequence of the present invention is inserted, optionally in conjunction with further regulatory elements, within the T-DNA of *Agrobacterium tumefaciens* or adjacent to it. All of the regulatory elements of the present invention may be autologous or heterologous to the cell to be transformed.

The present invention relates in a further embodiment to a host cell transformed with any one of the above mentioned vectors, in particular to a bacterial, yeast or plant cell, for instance a monocot or dicot host cell. In a particularly preferred embodiment, these host cells contain expressible and functional, preferably wild type, ASK-genes to be blocked or inhibited with respect to their expression by the transformed antisense or co-suppression construct.

In the context of the present invention, a number of terms shall be utilised as follows.

The term "promoter" refers to a sequence of DNA, usually up-stream (5') to the ASK-gene derived nucleic acid sequence in antisense or sense orientation, which controls the antisense or sense expression of ASK-gene derived nucleic acid sequence by providing the recognition for RNA polymerase and/or other factors required for transcription to start at the correct site. Promoter sequences are necessary, but not always sufficient, to drive the expression of the ASK-gene. In these cases, additional enhancer elements are used.

A "3' regulatory element" (or "3' end") refers to that portion of a gene comprising a DNA segment, excluding the 5' sequence which drives the initiation of transcription and the structural portion of the gene that contains a polyadenylation signal and any other regulatory signals capable of affecting messenger RNA (mRNA) processing or gene expression. The polyadenylation signal is usually characterised by affecting the addition of polyadenylic acid tracts to the 3' end of the mRNA precursor. Polyadenylation signals are commonly recognised by the presence of homology to the canonical form 5'-AATAAA-3', although variations are not uncommon.

The term "nucleic acid sequence" refers to a natural or synthetic polymer of DNA or RNA which may be single or double stranded, alternatively containing synthetic, non-natural or altered nucleotide bases capable of incorporation into DNA or RNA polymers. The nucleic acid sequence may be cDNA, genomic DNA, or RNA, for instance mRNA.

The term "gene" refers to a DNA sequence that codes for a specific protein and the DNA sequences regulating the expression of the coding sequence.

The term "regulatory element" refers to a sequence located upstream (5'), within and/or downstream (3') to a coding sequence whose transcription and expression is controlled by the regulatory element, potentially in conjunction with the protein biosynthetic apparatus of the cell. "Regulation" or "regulate" refer to the modulation of the gene expression induced by DNA sequence elements located primarily, but not exclusively, upstream (5') from the transcription start of the gene of interest. Regulation may result in an all or none response to a stimulation, or it may result in variations in the level of gene expression.

The term "coding sequence" refers to that portion of a gene encoding a protein, polypeptide, or a portion thereof, and excluding the regulatory sequences which drive the initiation or termination of transcription. The coding sequence or the regulatory element may be one normally found in the cell, in which case it is called "autologous" or "endogenous", or it may be one not normally found in a cellular location, in which case it is termed a "heterologous gene" or "heterologous nucleic acid sequence". A heterologous gene may also be composed of autologous elements arranged in an order and/or orientation not normally found in the cell in which it is transferred. A heterologous gene may be derived in whole or in part from any source known to the art, including a bacterial or viral genome or episome, eukaryotic nuclear or plasmid DNA, cDNA or chemically synthesised DNA.

The term "vector" refers to a recombinant DNA construct which may be a bacterial vector, in particular, plasmid, virus, or autonomously replicating sequence, phage or nucleotide sequence, linear or circular, of a single or double stranded DNA or RNA, derived from any source, in which a number of nucleotide sequences, in particular a promoter and the ASK-derived nucleic acid sequence have been joined or recombined into a unique construction which is capable of introducing a promoter fragment and the ASK-derived nucleic acid sequence in antisense orientation along with appropriate 3' untranslated sequence into a cell, in particular a plant cell.

As used herein, "plant" refers to photosynthetic organisms, such as whole plants including algae, mosses, ferns and plant-derived tissues. "Plant derived tissues" refers to differentiated and undifferentiated tissues of a plant, including roots, shoots, shoot meristems, coleoptilar nodes, tassels, leaves, cotyledonous petals, pollen, ovules, tubers, seeds, kernels and various forms of cells in culture such as intact cells, protoplasts, embryos and callus tissue. Plant-derived tissues may be in planta, or in organ, tissue or cell culture.

A "monocotyledonous plant" refers to a plant whose embryos normally only have one cotyledon or organ that stores and absorbs food. A "dicotyledonous plant" refers to a plant whose embryos normally have two cotyledons.

As used herein, "transformation" refers to the process by which cells, tissues or plants acquire properties encoded on a nucleic acid molecule that has been transferred to the cell, tissue or plant.

"Transformation" and "transferring" refers to methods to transfer DNA into cells including, but not limited to, biolistic approaches such as particle bombardment, microinjection, permeabilising the cell membrane with various physical (e.g., electroporation) or chemical (e.g., polyethylene glycol, PEG) treatments; the fusion of protoplasts or *Agrobacterium tumefaciens* or rhizogenes mediated transformation. For the injection and electroporation of DNA in plant cells there are no specific requirements for the plasmids used. Plasmids such as pUC derivatives can be used. If whole plants are to be regenerated from such transformed cells, there should be a selectable marker. Depending upon the method for the introduction of desired genes into the plant cell, further DNA sequences may be necessary; if, for example, the Ti or Ri plasmid is used for the transformation of the plant cell, at least the right border, often, however, the right and left border of the Ti and Ri plasmid T-DNA have to be linked as flanking region to the genes to be introduced.

If Agrobacteria are used for the transformation, the DNA to be introduced has to be cloned into specific plasmids, either into an intermediary vector or into a binary vector. The intermediary vectors can be integrated into the Ti or Ri plasmid of the Agrobacteria due to sequences that are homologous to sequences in the T-DNA by homologous recombination. The Ti or Ri plasmid furthermore contains the vir region necessary for the transfer of the T-DNA into the plant cell. Intermediary vectors cannot replicate in Agrobacteria. By means of a helper plasmid the intermediary vector can be transferred by means of a conjugation to *Agrobacterium tumefaciens*. Binary vectors can replicate both in *E.coli* and in Agrobacteria and they contain a selection marker gene and a linker or polylinker framed by the right and left T-DNA border region. They can be transformed directly into the Agrobacteria (Holsters et al., 1978). The *Agrobacterium* serving as a host cell should contain a plasmid carrying a vir region. The *Agrobacterium* transformed is used for the transformation of plant cells. The use of T-DNA for the transformation of plant cells has been extensively examined and described in EP-A 120 516; Hoekema, (1985); An et al., (1985).

For the transfer of the DNA into the plant cell, explants can be co-cultivated with *Agrobacterium tumefaciens* or *Agrobacterium rhizogenes*. From the infected plant material (e.g., pieces of leaf, stem segments, roots, but also protoplasts or plant cells cultivated by suspension) whole plants can be regenerated in a suitable medium, which may contain antibiotics or biozides for the selection of transformed cells.

Alternative systems for the transformation of monocotyledonous plants are the transformation by means of electrically or chemically induced introduction of DNA into protoplasts, the electroporation of partially permeabilised cells, the macroinjection of DNA into flowers, the microinjection of DNA into micro-spores and pro-embryos, the introduction of DNA into germinating pollen and the introduction of DNA into embryos by swelling (Potrykus, Physiol. Plant (1990), 269–273).

While the transformation of dicotyledonous plants via Ti plasmid vector systems with the help of *Agrobacterium tumefaciens* is well-established, more recent research work indicates that monocotyledonous plants are also accessible for transformation by means of vectors based on *Agrobacterium* (Chan et al., (1993); Hiei et al., (1994); Bytebier et al., (1987); Raineri et al., (1990), Gould et al., (1991); Mooney et al., (1991); Lit et al., (1992)).

In fact, several of the above-mentioned transformation systems could be established for various cereals: the electroporation of tissues, the transformation of protoplasts and the DNA transfer by particle bombardment in regenerative tissue and cells (Jahne et al., (1995). The transformation of wheat has been frequently described in the literature (Maheshwari et al., (1995). The transformation of maize has been described in Brettschneider et al., (1997) and Ishida et al., (1996).

The term "host cell" refers to a cell which has been genetically modified by transfer of a heterologous or autologous ASK-gene derived nucleic acid sequence or its descendants still containing this sequence. These cells are also termed "transgenic cells".

The term "operably linked" refers to the chemical fusion of two of more fragments of DNA in a proper orientation such that the fusion preserves or creates a proper reading frame, or makes possible the proper regulation of expression of the DNA sequences when transformed into plant tissue.

The term "expression" as used herein is intended to describe the transcription and/or coding of the sequence for the gene product. In the expression, a DNA chain coding for the sequence of the ASK-gene product is first transcribed to a complementary RNA, which is often an mRNA, and then the thus transcribed mRNA is translated into the above mentioned ASK gene product if the gene product is a protein. However, expression also induces the transcription of DNA inserted in antisense orientation to its 5' regulatory elements. Expression, which is constitutive and possibly further enhanced by an externally controlled promoter fragment thereby producing in a preferred embodiment multiple copies of antisense mRNA.

A "tissue specific promoter" refers to a sequence of DNA that provides recognition signals for RNA polymerase and/or other factors required for transcription to begin, and/or for controlling expression of the coding sequence precisely within certain tissues or within certain cells of that tissue. Expression in a tissue specific manner may be only in individual tissues, or cells within tissues, or in combinations of tissues. Examples may include tissue specific expression in embryos only and no other tissues within the plant, or may be in leaves, petals, ovules and stamen, and no other tissues of the plant. Here, "tissue specific" is also meant to describe an expression in a particular tissue or cell according to which the expression takes place mainly, but not exclusively, in the tissue.

"Selective expression" refers to expression mainly, preferably almost exclusively, in specific organs of the plant or embryo, including, but not limited to, cotyledons, endosperm, roots, leaves, tubers or seed. The term may also refer to expression at specific developmental stages in an organ, such as in early or late embryogenesis or in seedlings. In addition, "selective expression" may refer to expression in specific subcellular locations within the cell, such as the cytosol or vacuole.

The present invention thus relates to the above identified DNA constructs, in particular sense and antisense constructs comprising at least one regulatory element operably linked in antisense or sense orientation to a nucleic acid sequence derived from an ASK-gene of group II, to a vector comprising the DNA construct according to the above and to genetically modified cells containing at least one DNA construct or vector according to the above. These cells may in a particularly preferred embodiment be plant or yeast cells, in particular cells from monocotyledonous or dicotyledonous plants.

The present invention also relates to a plant comprising at least one cell being genetically modified as explained above, in particular comprising a DNA construct of the present invention. In particular, the present invention relates to a plant produced according to the process of the present invention, that is, to a plant which is obtained by transforming at least one plant cell with at least one DNA construct comprising a nucleic acid sequence derived from at least one ASK-gene of group II and wherein the transformed plant cell is cultivated and regenerated to a plant able to produce embryos which exhibit the above identified modified development. Both cultivation and regeneration may be carried out using conventional protocols such as described in Bechtold and Pelletier, 1998. Thus, the plant of the present invention is characterised by the presence of a DNA construct of the present invention in the nucleus, mitochondria or plastids of at least one of its cells, in particular the genome of at least one of its cells. In a further particularly preferred embodiment the plant is characterised by the specific and unexpected ability of its gametes to form upon fertilisation embryos exhibiting a modified development. Thus, in the context of the present invention, the wording a transgenic plant, the seeds of which comprise an embryo exhibiting a modified development refers to a transgenic plant being able to produce gametes which upon fertilisation form embryos exhibiting a modified development.

Thus, the present invention relates to plants comprising genetically modified cells according to the present invention and being capable of producing gametes which upon fertilisation form embryos exhibiting, at least in homozygous genetic background, a modified development. The present invention also relates to seeds, embryos, seedlings, calluses, cotyledons, petioles and plant tissue derived from such a plant or used to produce the plant and still comprising at least one of the genetically modified cells of the present invention. Thus, the present invention relates to plants, seeds, seedlings, cotyledons, plant parts and embryos non-biologically transformed, which possess, stably or transiently integrated in the genome of the cells, a sense or antisense construct according to the present invention enabling the production of non-variety specific gametes forming upon fertilisation seeds exhibiting the modified development.

Thus, the present invention also relates to transgenic plants, parts of plants, plant tissue, plant seeds, plant embryos, plant seedlings, plant propagation material, plant harvest material, plant leaves and plant pollen, plant roots containing the above identified plants cell of the present invention. These plants or plant parts are characterised by, as a minimum, the presence of the heterologous transferred DNA construct of the present invention in the genome or, in cases where the transferred nucleic acid molecule is autologous to the transferred host cell, are characterised by additional copies of the nucleic acid molecule of the present invention and/or a different location within the genome. Thus, the present invention also relates to plants, plant tissues, plant seeds, plant seedlings, plant embryos, propagation material, harvest material, leaves, pollen, roots, calluses, tassels etc. non-biologically transformed which possess stably or transiently integrated in the genome of the cells, for instance in the cell nucleus, plastids or mitochondria a heterologous and/or autologous nucleic acid sequence containing a regulatory element recognised by the polymerases of the cells of the said plant and, in a preferred embodiment, being operably linked to an ASK-derived sequence. The teaching of the present invention is therefore applicable to any plant, plant genus or plant species wherein the regulatory elements mentioned above are recognised by the polymerases of the cell. Thus, the present invention provides plants of many species, genuses, families, orders and classes that are ably to recognise these regulatory elements of the present invention or derivatives or parts thereof.

Any plant is considered, in particular plants of economic interest, for example plants grown for human or animal nutrition, plants grown for the content of useful secondary metabolites, plants grown for their content of fibres, trees and plants of ornamental interest. Examples which do not imply any limitation as to the scope of the present invention are corn (maize), wheat, barley, rice, sorghum, sugarcane, sugarbeet, soybean, Brassica, sunflower, carrot, tobacco, lettuce, cucumber, tomato, potato, cotton, Arabidopsis, Lolium, Festuca, Dactylis, or poplar.

The present invention also relates to a process, in particular a microbiological process and/or technical process, for producing a plant or reproduction and harvest material of said plant, including an heterologous or autologous DNA construct of the present invention stably or transiently integrated therein, and capable of being expressed in said plants or reproduction material, which process comprises transforming cells or tissue of said plants with a DNA construct containing a nucleic acid molecule of the present invention, i.e. a regulatory element which is capable of causing the stable integration of said nucleic acid molecules in said cell or tissue and enabling the expression of an operably linked further nucleic acid molecule in said plant cell or tissue, regenerating plants or reproduction material of said plant or both from the plant cell or tissue transformed with said DNA construct and, optionally, biologically replicating said last mentioned plants or reproduction material or both.

Needless to say, the teaching of the present invention is therefore applicable to any plant, plant genus or plant species containing ASK-genes or related genes whose expression may be inhibited by the transposable element containing constructs, the antisense or sense constructs of the present invention. Thus, the present invention provides a non-variety specific teaching.

The present invention also relates to the use of nucleic acid sequences derived from an ASK-gene of group II for preparing transgenic plants forming seeds the embryos of which exhibit a modified development.

The present invention will now be more specifically described with the following examples and the accompanying figures.

SEQ ID No. 1 to 5 represent oligonucleotide primers used to generate ASK specific DNA fragments, and for their detection in transformed plants.

EXAMPLE 1

Production of ASK-antisense Arabidopsis Plants:

Arabidopsis thaliana ecotype Columbia Co was used as wild-type in the experiment. Arabidopsis plants were grown at long-day photo period (16/8 hours), 21/18° C. (day/night) in a greenhouse or in culture chambers.

ASK gene-specific probes were obtained by PCR amplification of 5' non-conserved region of cloned ASK cDNAs. In situ hybridisation was performed as described (Domelas et al., 1999) using sense and antisense gene-specific RNA probes labelled with dioxygenin-11-UTP (Boehringer Mannheim). Signals were detected by calorimetric assay using anti-DIG IgG coupled to alkalyne phosphatase and NBT/BCIP as substrate.

Arabidopsis Columbia Co. plants were transformed (Bechtold and Pelletier (1998)) using *Agrobacterium tumefaciens* containing antisense constructs including fragments from the 5' extremity of the ASK-genes, obtained by PCR (Dornelas et al., 1999). ASK gene-specific probes were obtained using PCR-generated fragments of ca. 300 bp corresponding to the 5'-untranslated region and part of the N-terminal coding region of ASK cDNAs. The following synthetic oligonucleotide pairs were used as primers:

ASKSζ: 5'-TACTCTAGAAGTGAGAGAGAGAAGT-3' (SEQ ID No. 1);
and 5'-GTTCGGCCATCGATCTMTGGTCTG-3'(SEQ ID No.2);

ASKSη: 5'-CTATCTAGAGGCTTCCCTTTCTCTC-3' (SEQ ID No. 3);
and 5'-GCTCCGCCATCGATCTAATTGTCTG-3'(SEQ ID No. 4).

PCR reactions were carried out using 1 ng of ASK cDNA as a template and the following reaction conditions: initial denaturation at 94° C. for 2 min., followed by 35 cycles of 94° C./30s, 45°/30s and 72° C./1 min. PCR products were cloned as XbaI-ClaI fragments into the pBlueScript (Stratagene) vector (FIG. 3) and sequenced on both strands to check for polymerase induced errors.

Figure 3:
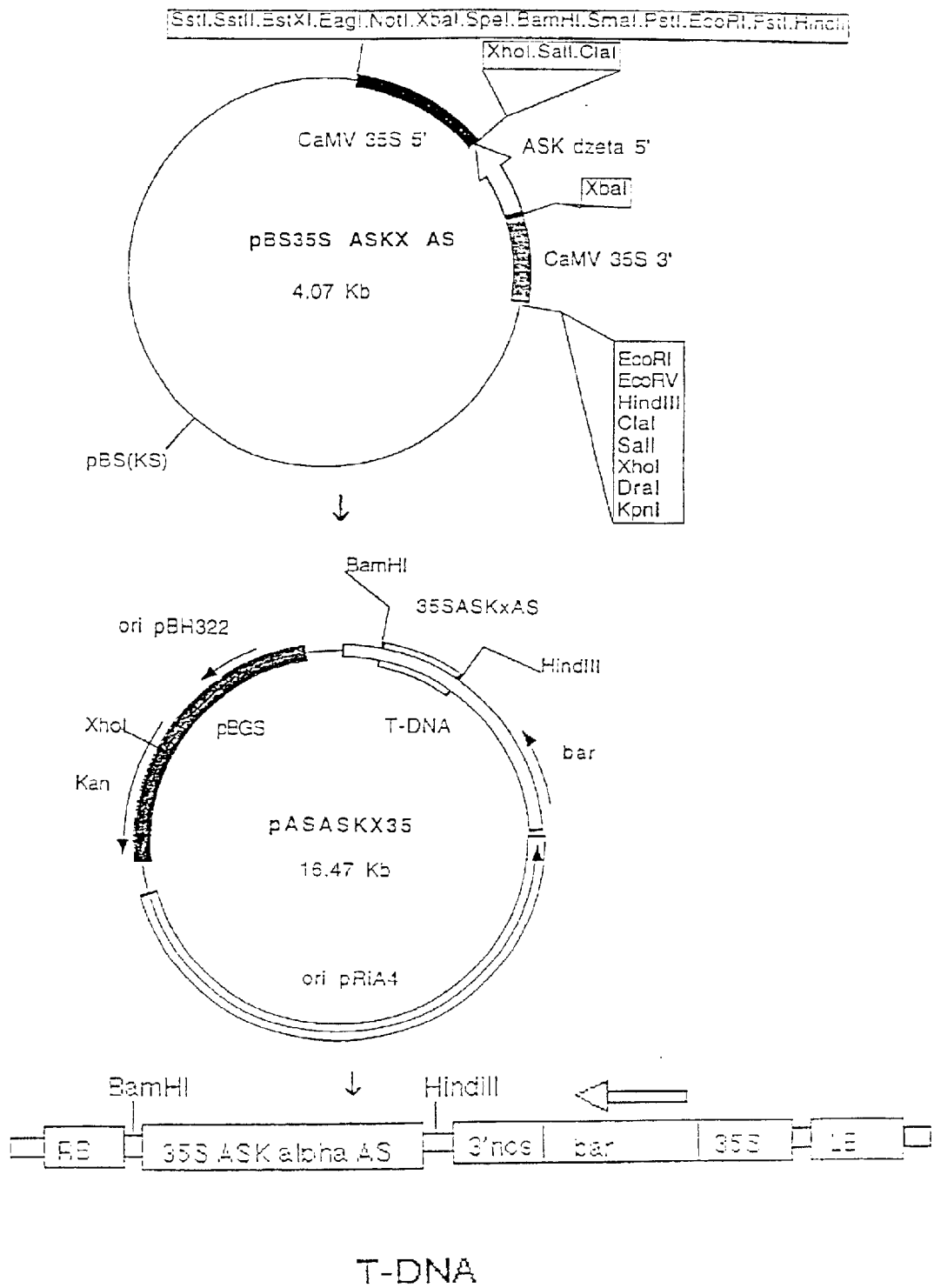
FIG. 3 shows the cloning scheme for obtaining the ASKdzeta antisense construct.

These fragments were cloned in antisense orientation under the strong constitutive CaMV 35S promoter, in a modified version of the *Agrobacterium tumefaciens* pEC plasmid (INRA, Versailles, France plasmid map, FIG. 3). FIG. 3 shows the cloning scheme indicating that the ASKdzeta 5' region defined above is cloned in antisense orientation to the 35S CaMV promoter and is functionally linked to the 35S CaMV 3' transcription termination region (construct: ASK αAS). The expression cassette obtained is cloned together with the bar gene between the left and right border sequence of *Agrobacterium tumefaciens*. At least 18 plants were obtained for each of the ASK antisense constructs. Transformation, cultivation and regeneration were carried out using standard protocols. Transformed plants were left to self-pollinate and the progeny was tested for the presence of the construct insertion by PCR using primers in the ASK genes in combination with the TAG 17 primer on the pEC T-DNA DNA (5'-GAGCCGCAGGAA-CCGCAGGAGTGCA-3', SEQ ID No. 5). The amount of native ASK (about 1,6 kbp) and antisense (about 0,3 kbp) transcript levels was accessed by Northern blot experiments, using ASK gene-specific probes under the conditions described in Dornelas et al., 1999.

In order to assess the effect of the reduction of transcript levels of both ASK-genes simultaneously, more than 40 independent crosses were performed among homozygous ASK antisense plants. Embryos carrying both ASK antisense constructs were obtained by crossing homozygous ASKetha and -dzeta antisense plants.

EXAMPLE 2

Embryo development of ASKdzeta antisense embryos showed abnormal development as early as the first divisions of the suspensor. The uppermost suspensor cell showed features comparable to the cells of the embryo proper cells such as having less vacuolated cytoplasm and similar cell shape. As the first longitudinal divisions in the apical cell took place to produce a guardant embryo proper, an abnormal, longitudinal cell division of the uppermost suspensor cell (the hypophyseal cell) occurred. In the wild-type embryos the uppermost suspensor cell exclusively undergoes transversal mitotic divisions and only at the early globular stage to form the hypophysis.

The ASKζ antisense embryos showed abnormal development as early as the first divisions of the suspensor. The uppermost suspensor cell showed features comparable to the cells of the embryo proper cells such as having less vacuolated cytoplasm and similar cell shape. As the first longitudinal divisions in the apical cell took place to produce a quadrant embryo proper, an abnormal, longitudinal cell division of the uppermost suspensor cell (the hypophyseal cell) occurred. In the wild-type embryos the uppermost suspensor cell exclusively undergoes transversal mitotic divisions and only at the early globular stage to form the hypophysis.

At the guardant stage of the ASKdzeta embryo development, the mitotic transversal divisions of the embryo proper cells proceeded. Simultaneously, the daughter cells resulting from the abnormal cell division of the hypophyseal cell mimicked the division patterns highly characteristic of the terminal embryonic cell. As a result of these aberrant division patterns, the embryo proper contained twice as many cells when compared to the wild-type. At the dermatogen state, the cells derived from the hypophyseal cell underwent periclinal divisions, giving rise to protoderm-like cells from this stage onwards. The latter cells divided only anticlinally, behaving like protoderm cells. At the globular stage of the ASKdzeta antisense embryo development, the second uppermost suspensor cell had undergone transverse division and formed a hypophysis-like structure. Altogether, these aberrant cell divisions resulted in an embryo showing an ovoidal rather than a globular shape.

Figure 1:
FIG. 1 shows a mature antisense embryo.

Both in the wild-type as in the ASKdzeta antisense embryos, at the late globular to heart stage protodermal divisions increased in frequency at the site of the future cotyledons. These cell divisions resulted in a triangular shaped embryo. The cotyledon initials which were formed at the apical region of the ASKdzeta antisense embryo were supernumerary in most cases (70% of the embryos analyzed, n>100). Thus, when cells that will form the cotyledons are recruited at the late globular stage of ASKdzeta antisense embryos, as much as twice the amount of cells were available. Consequently, up to six cotyledons were detected in mature ASKdzeta antisense embryos (FIG. 1). At the torpedo stage, the supernumerary cotyledons were visible in cleared seeds. With further elongation of the cotyledons and the bending of the embryo, the seeds of the ASKdzeta antisense plants showed a roundish shape when compared to the wild-type, due to the accommodation of the supernumerary cotyledons.

Figure 2:
FIG. 2 shows an antisense seedling.

After germination of ASKdzeta antisense seedlings displayed a normal shape, except that they showed an inceased number of cotyledons (polycotyly) (FIG.2). Ninety percent of the seedings presenting polycotyly showed 3 cotyledons, while ten percent showed 4–6 cotyledons. In this latter case, cotyledons, were reduced in size. The relative position of the first leaves. Which alternate with the insertion of cotyledons, was maintained in the ASKdzeta antisense plants.

EXAMPLE 3

Embryo Development of ASKTη Antisense Plants

As described in example 2, an early developmental defect was also detected during the first mitotic divisions of the ASKetha antisense embryos. The uppermost suspensor cell of the latter embryo had less vacuolated cytoplasm and the shape of the embryo proper cells. After the first longitudinal division of the embryo proper cell, the hypophyseal cell divided abnormally (i.e. longitudinally) and the adjacent suspensor cell became less vacuolized. At the guardant stage, the daughter cell resulting from normal division of the hypophyseal cell occasionally divided again and the adjacent suspensor cell underwent an abnormal, longitudinal division.

At the globular stage of the ASKetha antisense embryos, the embryo proper cell had not differentiated into typical protodermal cells as it is observed in the wild-type embryos at this stage. Instead further abnormal mitotic divisions of the suspensor proceeded towards the lower cells. AT the late-globular stage, the embryo proper cell divided irregularly and the suspensor cells divided further, causing the ASKetha antisense embryo to adopt a club-shaped form. At this stage, ASKetha antisense plants showed 70–100% seed abortion.

EXAMPLE 4

Embryo Development of ASKetha and ASKdzeta Antisense Plants

In order to assess the effect of the reduction of both ASKdzeta and ASKetha transcript levels simultaneously, homozygous ASKdzeta and ASKetha antisense plants were crossed. Double ASKdzeta/etha antisense embryos showed abnormal cell divisions, starting from the first division of the apical cell. The division planes of both basal and apical cells varied in a great extent. The ASKdzeta/etha antisense embryos failed to develop further than the globular stage and the seeds aborted. The phenotype of the double ASKdzeta/etha antisense embryo is thus more severe than the transcript levels of each individual gene are reduced. This suggests that both genes may act in different pathway to transduce signals that are essential for the progression of Arabidopsis embryo development beyond the globular stage.

References Cited

An et al., EMBO J. 4 (1985), 277–287.
Angenent et al., Plant Cell 7 (1995), 1569–1582.
Bechtold and Pelletier, Methods Mol. Biol. 82, (1998), 259–266.
Brettschneider et al., Theor. Appl. Genet. 94 (1997), 737–748.
Bytebier et al., Proc. Natl. Acad. Sci. USA 84 (1987), 5345–5349.
Chan et al., Plant Mol. Biol. 22 (1993) 491–506.
Dornelas et al., Gene 212 (1998), 249–257.
Dornelas et al., Plant Mol. Biol. 39 (1999), 137–147.
Gould et al., Plant Physiol. 95 (1991), 426434.
Hiei et al., Plant J. 6 (1994), 271–282.
Hoekema: The Binary Plant Vector System, Offsetdrukkerij Kanters B. V.,
Alblasserdam (1985), Chapter V.
Holsters et al., Mol. Gen. Genet. 163 (1978), 181–187.
Ishida et al., Nature Biotechnology 14 (1996), 745–750.
Jähne et al., Eurphytica 85 (1995), 3544.
Lit et al., Plant Mol. Biol. 20 (1992), 1037–1048.
Maheshwari et al., Critical Reviews in Plant Science 14 (2) (1995), 149–178.
Mooney et al., Plant Cell Tiss. & Org. Cult. 25 (1991), 209–218.
Potrykus, Physiol. Plant (1990), 269–273.
Raineri et al., Bio/Technology 8 (1990), 33–38.
Rounsley et al., Plant Cell 7 (1995), 1259–1269
Thoma et al., Plant Physiol. 105 (1994), 35–45.
Tichtinsky et al., Biochimica et Biophysica Acta 1442 (1998), 261–273).

---

What is claimed is:

1. A process for the production of a transgenic plant, the seeds of which comprise an embryo exhibiting a modified cotyledons development, the process comprising the steps of:

transforming at least one plant cell with at least one nucleic acid construct comprising an antisense of at least 150 nucleobases in length which specifically targets and inhibits the expression of ASKdzeta (ASKζ)-gene of group II of SEQ ID NO: 6 150 base pairs corresponding to the 5' untranslated region and part of the N-terminal, and forming, from said transformed cells, a plant whose embryos exhibit modified development characterized by the development of an increased number of cotyledons.

2. The process according to claim 1, wherein the antisense, comprises at least 300 nucleobases.

3. The process according to claim 2, wherein the antisense specifically targets the 5' untranslated region and part of the N-terminal coding region of SEQ ID NO: 6.

4. The process acording to claim 1, wherein the antisense comprises 150 to 350 nucleobases which specifically targets the 5'-untranslated region and a part of the N-terminal coding region of ASKdzeta (ASKζ)-gene of group II.

5. The process according to claim 1, wherein the ASK-gene is in the form of a cDNA or genomic DNA.

6. The process according to claim 1, wherein the nucleic acid construct comprises at least one regulatory element operably linked to the antisense and directs the expression of the antisense sequence.

7. The process according to claim 6, wherein the regulatory element is a promoter and/or enhancer.

8. The process according to claim 1, wherein the nucleic acid construct comprises a transcription termination signal operably linked to the antisense sequence.

9. The process according to claim 1, wherein the nucleic acid construct is cloned into a plasmid or viral vector.

10. The process according to claim 1, wherein the plant cell is from a monocotyldonous or dicotyledonous plant.

11. The process accoding to claim 10, wherein the monocotyledonous or dicotyledonous plant is Arabidopsis, brassica, cotton, potato, soya, sugar beet, sugar cane, an ornamental plant, rice, maize, barley or wheat.

12. A plant comprising at least one cell according to claim 10.

13. Seeds amd plant derived tissue comprising a genetically modified cell according to claim 12.

14. The process according to claim 1, wherein the plant cell is transformed by transfer of the nucleic acid, consbruct by a method selected from the group comprising: transfer via a bacterium, transfer via virus to the cell, transfer via direct uptake of the DNA contuct by microinjection of the DNA constrct, transfer via direct uptake of the DNA construct by particle bombardment.

15. The proess according to claim 1, wherein the transformed cell is regnerated into a differentiated plant.

16. A plant produced according to the process of claim 1.

17. Seeds and plant derived tissue obtained from a plant produced by the process according to claim 1.

18. The process according to claim 1, wherein the antisense specifically targets the 5' untranslated region and part of the N-terminal coding region of SEQ ID NO: 6.

19. The process according to claim 1, wherein the antisense comprises between 150 and 300 nucleobases.

20. The process according to claim 1, wherein the regulatory element comprises a 35-S CaMV-promoter.

21. The process according to claim 1, wherein the transcription termination signal comprises a poly A site.

22. A transgenic Arabidopsis plant, the seeds of which comprise an embryo exhibiting a modified cotyledons development, which plant comprises at least one plant cell transformed by a nucleic acid construct comprising an antisense of at least 150 nucleobases in length which specifically targets and inhibits the expression of ASKdzeta (ASKζ)-gene of group II of SEQ ID NO: 6, wherein at least on embryo exhibits the modified cotaledons development.

* * * * *

UNITED STATES PATENT AND TRADEMARK OFFICE
CERTIFICATE OF CORRECTION

PATENT NO. : 6,822,139 B1
DATED : November 23, 2004
INVENTOR(S) : M. Dornelas et al.

It is certified that error appears in the above-identified patent and that said Letters Patent is hereby corrected as shown below:

Column 1,
Line 57, "forwhich" should read -- for which --.

Column 2,
Line 41, "ASKene" should read -- ASK-gene --.

Column 3,
Line 52, "shaqqy-like" should read -- shaggy-like --.

Column 4,
Line 21, "ASKdzetha" should read -- ASKdzeta --.
Line 24, "ASKdzetha" should read -- ASKdzeta --.
Line 27, "suspensorlembryo" should read -- suspensor/embryo --.
Line 29, "ASKdzetha" should read -- ASKdzeta --.
Line 48, "ASKgene" should read -- ASK-gene --.

Column 5,
Line 67, "andlor" should read -- and/or --.

Column 8,
Line 1, "andlor" should read -- and/or --.

Column 9,
Line 39, "(Jahne et al., (1995)." should read -- Jähne et al., (1995)). --.

Column 12,
Line 50, "5'-GTTCGGCCATCGATCTMTGGTCTG-" should read -- 5'-GTTCGGCCATCGATCTAATGGTCTG- --.

Column 13,
Line 4, "ASK αAS)." should read -- ASK α AS). --.

Column 14,
Line 24, "cotyledons, were" should read -- cotyledons were --.
Line 25, "leaves. Which" should read -- leaves, which --.

Column 15,
Line 1, "pathways" should read -- pathway --.
Line 16, "Domelas et al." should read -- Dornelas et al., --.
Line 17, "426434." should read -- 426-434. --.

UNITED STATES PATENT AND TRADEMARK OFFICE
CERTIFICATE OF CORRECTION

PATENT NO.    : 6,822,139 B1
DATED         : November 23, 2004
INVENTOR(S)   : M. Dornelas et al.

It is certified that error appears in the above-identified patent and that said Letters Patent is hereby corrected as shown below:

Column 16,
Lines 2-3, do not break "Kanters B.V., Alblasserdam (1985), Chapter V."
Line 6, "3544." should read -- 35-44. --.

Column 19,
Lines 20-23, "6 150 base pairs corresponding to the 5' untranslated region and part of the N-terminal, and" should read -- 6, and --.
Line 28, "antisense, comprises" should read -- antisense comprises --.
Line 50, "monocotyldonous" should read -- monocotyledonous --.

Column 20,
Line 17, "amd" should read -- and --.
Line 20, "acid, consbruct" should read -- acid construct --.
Line 23, "contuct" should read -- construct --.
Line 21, "constrct" should read -- construct --.
Line 49, "on embryo" should read -- one embryo --.
Line 49, "cotaledons" should read -- cotyledons --.

Signed and Sealed this

Eighteenth Day of October, 2005

JON W. DUDAS
*Director of the United States Patent and Trademark Office*

SEQUENCE LISTING

<160> NUMBER OF SEQ ID NOS: 6

<210> SEQ ID NO 1
<211> LENGTH: 25
<212> TYPE: DNA
<213> ORGANISM: Arabidopsis sp.

<400> SEQUENCE: 1
tactctagaa gtgagagaga gaagt                     25

<210> SEQ ID NO 2
<211> LENGTH: 25
<212> TYPE: DNA
<213> ORGANISM: Arabidopsis sp.

<400> SEQUENCE: 2
gttcggccat cgatctaatg gtctg                     25

<210> SEQ ID NO 3
<211> LENGTH: 25
<212> TYPE: DNA
<213> ORGANISM: Arabidopsis sp.

<400> SEQUENCE: 3
ctatctagag gcttcccttt ctctc                     25

<210> SEQ ID NO 4
<211> LENGTH: 25
<212> TYPE: DNA
<213> ORGANISM: Arabidopsis sp.

<400> SEQUENCE: 4
gctccgccat cgatctaatt gtctg                     25

<210> SEQ ID NO 5
<211> LENGTH: 25
<212> TYPE: DNA
<213> ORGANISM: Arabidopsis sp.

<400> SEQUENCE: 5
gagccgcagg aaccgcagga gtgca                     25

<210> SEQ ID NO 6
<211> LENGTH: 1636
<212> TYPE: DNA
<213> ORGANISM: Arabidopsis sp.
<220> FEATURE:
<221> NAME/KEY: mRNA
<222> LOCATION: (1)..(1636)
<223> OTHER INFORMATION: strain Columbia ecotype
    taxon:3702
    tissue type leaves
    clone lib lambda ZAPII  development stage young shoots
<300> PUBLICATION INFORMATION:
<301> AUTHORS: Dornelas, M.C., Schwebel-Dugue,N., Thomas, M., Lecharny,
    A. and Kreis, M.
<302> TITLE: Three New cDNAs Related to SGG/GSK-3 ( Shaggy/Glycogen
    Synthase Kinase-3) from Arabidopsis thaliana ( Accession No.
    X94938, x94939 and X99696) ( PGR97-008)
<303> JOURNAL: Plant Physiol.
<304> VOLUME: 113
<305> ISSUE: 1
<306> PAGES: 306-306
<307> DATE: 1997-01-01
<308> DATABASE ACCESSION NUMBER: genbank/X94938
<309> DATABASE ENTRY DATE: 1998-02-13
<313> RELEVANT RESIDUES: (1)..(1636)

<400> SEQUENCE: 6

| | | | | | |
|---|---|---|---|---|---|
| tttactcttt | cagtgagaga | gagaagttag | agctgtaaaa | gcacatgact | tcgataccat | 60 |
| tggggcctcc | tcagcctccg | tctttagctc | ctcagccgcc | gcatcttcac | ggcggagatt | 120 |
| ctttgaaacg | tcgtcccgat | atagacaacg | acaaggaaat | gtctgctgct | gttatagaag | 180 |
| gaaatgatgc | tgttaccggt | cacataattt | ctactacaat | tggagcaaa | aatggtgaac | 240 |
| ctaaacagac | cattagttac | atggccgaac | gtgttgttgg | aacaggatca | ttcggaattg | 300 |
| tattccaggc | aaaatgcttg | gaaactggag | aatcagtagc | cattaagaag | gttttgcaag | 360 |
| atcgccgtta | taaaaaccga | gagttgcaat | taatgcgact | aatggaccat | ccaaatgtgg | 420 |
| tttccttgaa | gcattgtttc | ttctctacaa | cgactagaga | tgagctcttc | ctcaatctcg | 480 |
| ttatggagta | tgtaccagag | acattgtacc | gggttttgaa | gcactatact | agttcaaacc | 540 |
| agcggatgcc | tatcttctat | gtcaaacttt | acacatacca | aatcttcaga | ggcttggctt | 600 |
| atatccatac | tgctcctggt | gtctgccaca | gagatataaa | accacaaaat | cttttggttg | 660 |
| atccccacac | ccatcagtgt | aagctctgtg | attttggaag | tgcaaaagta | ctggtgaaag | 720 |
| gtgaaccaaa | catatcatat | atctgctctc | ggtattaccg | agctccagaa | ctcatctttg | 780 |
| gtgccacaga | gtatacatca | tccattgata | tatggtctgc | tggttgtgtt | ctggcagagc | 840 |
| tacttcttgg | gcagccgtta | ttcccgggag | aaaattctgt | ggaccagcta | gtggagatca | 900 |
| taaaggttct | tggtactcca | actcgcgaag | aaatccggtg | catgaaccca | aactacacag | 960 |
| acttcagatt | cccacaaatc | aaagcccacc | cttggcataa | ggttttccac | aagcggatgc | 1020 |
| ctccggaagc | cattgacctt | gcatctcggc | ttcttcaata | tcaccaagt | ctacgttgca | 1080 |
| ctgcgctcga | ggcatgtgcg | catccgtttt | tcaatgaact | ccgtgagcca | aatgctcgtc | 1140 |
| ttccaaatgg | ccgacctcta | ccaccgttgt | tcaacttcaa | acaagagttg | tctgggctt | 1200 |
| caccggagct | tatcaacagg | ctaataccag | agcatgtgag | gcgacagatg | aatggtggct | 1260 |
| ttccatttca | agctggaccc | tagaaaagcg | atctcgagat | gcttttccag | agcaaaatgc | 1320 |
| cgccttatgg | aatgaaggag | agggagattt | acttctctct | gattaactaa | gtatcagctt | 1380 |
| ctgagaagag | atgatgtctc | ctccttagac | gtggccaatt | cagcttttg | agaaatcagg | 1440 |
| aggcgatgat | tgtgtcccat | tataatcttt | ttgttcactg | acttgtagag | agatactttt | 1500 |

```
ctcctgtatc agtatttgta tatgtttttg tccttgaaat gaaacaaaat cgattccaaa    1560
aaaaaaaaaa aaaaaaaaaa aaaaaaaaaa aaaaaaaaaa aaaaaaaaaa aaaaaaaaaa    1620
aaaaaaaaaa aaaaaa                                                    1636
```